US010814316B2

(12) United States Patent
Lauritzen et al.

(10) Patent No.: US 10,814,316 B2
(45) Date of Patent: Oct. 27, 2020

(54) CATALYTIC PROCESS FOR CO-PRODUCTION OF BENZENE, ETHYLENE, AND HYDROGEN

(71) Applicant: SHELL OIL COMPANY, Houston, TX (US)

(72) Inventors: Ann Marie Lauritzen, Houston, TX (US); Ye-Mon Chen, Sugar Land, TX (US); Chi Chiang Lee, Sugar Land, TX (US)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 16/469,533

(22) PCT Filed: Dec. 13, 2017

(86) PCT No.: PCT/US2017/065949
§ 371 (c)(1),
(2) Date: Jun. 13, 2019

(87) PCT Pub. No.: WO2018/111955
PCT Pub. Date: Jun. 21, 2018

(65) Prior Publication Data
US 2020/0078778 A1   Mar. 12, 2020

Related U.S. Application Data

(60) Provisional application No. 62/434,913, filed on Dec. 15, 2016.

(51) Int. Cl.
| | | |
|---|---|---|
| *C07C 2/76* | (2006.01) | |
| *B01J 29/90* | (2006.01) | |
| *B01J 29/44* | (2006.01) | |
| *B01J 37/00* | (2006.01) | |
| *B01J 37/08* | (2006.01) | |
| *B01J 37/18* | (2006.01) | |
| *B01J 38/10* | (2006.01) | |
| *B01J 38/12* | (2006.01) | |

(52) U.S. Cl.
CPC .............. *B01J 29/90* (2013.01); *B01J 29/44* (2013.01); *B01J 37/0045* (2013.01); *B01J 37/08* (2013.01); *B01J 37/18* (2013.01); *B01J 38/10* (2013.01); *B01J 38/12* (2013.01); *C07C 2/76* (2013.01); *B01J 2229/186* (2013.01); *B01J 2229/36* (2013.01); *B01J 2229/40* (2013.01); *C07C 2521/04* (2013.01); *C07C 2521/08* (2013.01); *C07C 2521/12* (2013.01); *C07C 2523/42* (2013.01); *C07C 2529/44* (2013.01)

(58) Field of Classification Search
CPC ..... C07C 5/327; C07C 5/3332; C07C 5/3335; C07C 2/42; C07C 2/46
USPC ................... 585/417, 418, 660, 661
See application file for complete search history.

(56) References Cited

U.S. PATENT DOCUMENTS

| | | | |
|---|---|---|---|
| 4,899,006 | A | 2/1990 | Dave et al. |
| 5,053,570 | A | 10/1991 | Soto et al. |
| 5,227,557 | A | 7/1993 | Bournonville et al. |
| 7,186,871 | B2 | 3/2007 | Mitchell et al. |
| 7,186,872 | B2 | 3/2007 | Juttu et al. |
| 8,772,563 | B2 | 7/2014 | Lauritzen et al. |
| 8,871,990 | B2 | 10/2014 | Lauritzen et al. |
| 2006/0122446 | A1 | 6/2006 | Louret et al. |
| 2007/0249879 | A1 | 10/2007 | Iaccino et al. |
| 2008/0194891 | A1 | 8/2008 | Pretz et al. |
| 2011/0021853 | A1 | 1/2011 | Lauritzen et al. |
| 2011/0301394 | A1 | 12/2011 | Chen et al. |
| 2015/0321182 | A1 | 11/2015 | Madgavkar et al. |

FOREIGN PATENT DOCUMENTS

| | | |
|---|---|---|
| EP | 0244162 A1 | 11/1987 |
| WO | 2009105447 A1 | 8/2009 |

OTHER PUBLICATIONS

International Search Report and Written Opinion received for PCT Patent Application No. PCT/US2017/065949 dated Feb. 22, 2018, 8 pages.
Moorehead et al., "Microactivity Evaluation of FCC Catalysts in the Laboratory: Principles, Approaches and Applications", Fluid Catalytic Cracking: Science and Technology, vol. 76, 1993, pp. 223-255.
Young, "Realistic Assessment of FCC Catalyst Performance in the Laboratory", Fluid Catalytic Cracking: Science and Technology, vol. 76, 1993, pp. 257-282.

*Primary Examiner* — Thuan D Dang

(57) ABSTRACT

A process for the production of benzene and ethylene from an alkane-containing gas stream. The alkane-containing gas stream may be contacted, in a reaction zone of a reactor under alkane aromatization conditions, with an aromatization catalyst including any combination of fresh, spent, and regenerated catalyst to produce an outlet stream including (i) spent catalyst and (ii) a product mixture including benzene and ethylene. The spent catalyst may be regenerated in a regeneration zone under regeneration conditions to produce the regenerated catalyst. A selected amount of fresh catalyst may be added to the regeneration zone to produce the mixture of fresh catalyst and regenerated catalyst, which may be recycled to the reaction zone. A ratio of benzene to ethylene in the product mixture may be controlled by modifying the alkane aromatization conditions, the regeneration conditions, and/or the selected amount of fresh catalyst added to the regeneration zone.

10 Claims, No Drawings

CATALYTIC PROCESS FOR CO-PRODUCTION OF BENZENE, ETHYLENE, AND HYDROGEN

CROSS REFERENCE TO RELATED APPLICATIONS

This is a national stage application of International Application No. PCT/US2017/065949, filed 13 Dec. 2017, which claims benefit of priority to U.S. Provisional Application No. 62/434,913, filed 15 Dec. 2016.

FIELD OF THE INVENTION

This disclosed subject matter relates to a process for producing aromatic hydrocarbons and ethylene from lower alkanes in a reactor containing an aromatization catalyst which includes any combination of fresh, spent, and regenerated catalyst, and wherein the ratio of benzene to ethylene in the product stream is controlled by modifying the aromatization conditions, the regeneration conditions and/or the amount of fresh catalyst added to the catalyst mixture in the reaction zone.

BACKGROUND OF THE INVENTION

Ethylene and benzene are two key chemical building blocks for the worldwide petrochemical industry. There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformates produced through a catalytic reforming process and pyrolysis gasolines produced through a naphtha cracking process, from non-aromatic hydrocarbons using a solvent extraction process.

In an effort to meet growing world demand for key petrochemicals, various industrial and academic researchers have been working for several decades to develop catalysts and processes to make light aromatics, benzene, toluene, xylenes (BTX) from cost-advantaged, light paraffin (C1-C4) feeds. Catalysts devised for this application usually contain a crystalline aluminosilicate (zeolitic) material such as ZSM-5 and one or more metals such as Pt, Ga, Zn, Mo, etc. to provide a dehydrogenation function. Aromatization of ethane and other lower alkanes is thermodynamically favored at high temperature and low pressure without addition of hydrogen to the feed. Unfortunately, these process conditions are also favorable for rapid catalyst deactivation due to formation of undesirable surface coke deposits which block access to the active sites of the catalyst.

One approach to circumvent this rapid deactivation problem is to devise a lower alkane aromatization process featuring a fluidized catalyst bed in which catalyst particles cycle rapidly and continuously between a reaction zone where aromatization takes place and a regeneration zone where the accumulated coke is burned off the catalyst to restore activity. For example, U.S. Pat. No. 5,053,570 describes a fluid-bed process for converting lower paraffin mixtures to aromatics.

The best-known, commercially-practiced solution to the problem of making petrochemical building blocks from ethane involves thermal cracking of ethane to produce primarily ethylene and hydrogen, along with a number of byproducts including benzene and other aromatics. This ethane cracking process does not utilize a catalyst and requires temperatures of 750-800° C. to achieve economically viable conversion levels.

Due to the highly endothermic nature of the alkane aromatization reaction, there is a need to provide heat input (e.g., above what may be generated by burning product coke) to the reaction zone in order to maintain the required reaction temperature.

Therefore, there is a need to develop an improved direct, non-oxidative alkane aromatization process that provides for the necessary heat input and maximizes the desired co-production of benzene, ethylene, and hydrogen from lower alkanes.

SUMMARY OF THE INVENTION

According to an embodiment of the disclosed subject matter, a process for the production of benzene and ethylene from an alkane-containing gas stream is provided. The alkane-containing gas stream includes at least one of ethane, propane or butane, and the process may include (a) contacting the alkane-containing gas stream, in a reaction zone of a reactor under alkane aromatization conditions, with an aromatization catalyst including a mixture of fresh catalyst and regenerated catalyst to produce an outlet stream including (i) spent catalyst and (ii) a product mixture including benzene and ethylene. In step (b), the spent catalyst may be separated from the product mixture in the outlet stream. Step (c) may include regenerating the separated spent catalyst in a regeneration zone under regeneration conditions to produce the regenerated catalyst. A selected amount of fresh catalyst may be added to the regeneration zone to produce the mixture of fresh catalyst and regenerated catalyst in step (d). Next, in step (e), the mixture of fresh catalyst and regenerated catalyst may be recycled to the reaction zone. In step (f), a ratio of benzene to ethylene in the product mixture may be controlled by modifying at least one of: the alkane aromatization conditions, the regeneration conditions, and the selected amount of fresh catalyst added to the regeneration zone in step (d).

In an embodiment of the disclosed subject matter, a process for the production of benzene and ethylene from an alkane-containing gas stream is provided. The alkane-containing gas stream may contain at least one of ethane, propane or butane. The process may include (a) contacting the alkane-containing gas stream, in a reaction zone of a reactor under alkane aromatization conditions, with an aromatization catalyst comprising recycled spent catalyst and a mixture of fresh catalyst and regenerated catalyst to produce an outlet stream comprising (i) spent catalyst and (ii) a product mixture comprising benzene and ethylene. In step (b), the spent catalyst may be separated from the product mixture in the outlet stream. Step (c) may include regenerating a first portion of the separated spent catalyst in a regeneration zone under regeneration conditions to produce the regenerated catalyst. Next, in step (d), a selected amount of fresh catalyst may be added to the regeneration zone to produce the mixture of fresh catalyst and regenerated catalyst. In step (e), the mixture of fresh catalyst and regenerated catalyst may be recycled to the reaction zone. In step (f) a second portion of the separated spent catalyst may be recycled to the reaction zone. Next in step (g), a ratio of benzene to ethylene in the product mixture may be controlled by modifying at least one selected from the group consisting of: the alkane aromatization conditions, the regeneration conditions, and the selected amount of fresh catalyst added to the regeneration zone in step (d).

In another embodiment of the disclosed subject matter, a process for the production of benzene and ethylene from an alkane-containing gas stream. The alkane-containing gas stream contains at least of ethane, propane or butane. The disclosed process may include (a) contacting the alkane-containing gas stream, in a reaction zone of a reactor under alkane aromatization conditions, with an aromatization catalyst comprising regenerated catalyst and a mixture of fresh catalyst and spent catalyst to produce an outlet stream comprising (i) spent catalyst and (ii) a product mixture comprising benzene and ethylene. In step (b) the spent catalyst may be separated from the product mixture in the outlet stream. Next in step (c) a first portion of the separated spent catalyst may be regenerated in a regeneration zone under regeneration conditions to produce the regenerated catalyst. Step (d) may include recycling the regenerated catalyst to the reaction zone. In step (e) a selected amount of fresh catalyst may be added to a second portion of the separated spent catalyst to produce the mixture of fresh catalyst and spent catalyst. Next, in step (f) the mixture of fresh catalyst and spent catalyst may be recycled to the reaction zone. In step (g), a ratio of benzene to ethylene in the product mixture may be controlled by modifying at least one of: the alkane aromatization conditions, the regeneration conditions, and the selected amount of fresh catalyst added to the second portion of the separated catalyst in step (e).

The disclosed subject matter also provides several features and advantages. One of the features and advantages of the disclosed process includes utilization of an aromatization catalyst that produces benzene and ethylene as a function of catalyst age distribution. Another feature is the ability to add fresh catalyst and remove spent catalyst during reactor operation so that relative yields of benzene and ethylene may be altered. Yet another feature is the ability to provide the heat of reaction for producing benzene and ethylene. In addition, the process of the presently disclosed subject matter utilizes a catalyst that enables proportionately greater benzene production along with ethylene, at a lower temperature than that typically used in ethane crackers (680-700° C. vs. 750-800° C.). Because the ratio of benzene to ethylene production declines as the catalyst ages, the disclosed process provides flexibility for altering relative yields of benzene and ethylene by adjusting the relative amounts of fresh and aged catalyst in the reactor. In addition, the ratio of benzene to ethylene may be controlled by modifying the aromatization conditions and regeneration conditions. This results in significantly higher and economically more attractive alkane-containing gas stream conversion and benzene and ethylene yields.

Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

DETAILED DESCRIPTION

This presently disclosed subject matter is directed towards a processing scheme for producing aromatics and ethylene from an alkane-containing gas stream. The conversion of alkanes in the alkane-containing gas stream to aromatics is typically carried out in a reactor comprising a catalyst, which is active in the conversion of the alkanes to aromatics and ethylene.

The presently disclosed subject matter provides for the ability to utilize an aromatization catalyst that enables the production of different relative amounts of benzene and ethylene as a function of catalyst age. In addition, the process of the presently disclosed subject matter utilizes an aromatization catalyst that enables proportionately greater benzene production along with ethylene, at a lower temperature than that typically used in ethane crackers (680-700° C. vs. 750-800° C.). For the co-production of benzene and ethylene, the presently disclosed process provides the ability to add fresh catalyst and remove spent catalyst during reactor operation so that relative yields of benzene and ethylene may be altered. Because the ratio of benzene to ethylene production by the aromatization catalyst declines as the aromatization catalyst ages, the disclosed process provides flexibility for altering desired relative yields of benzene and ethylene by adjusting the relative amounts of fresh and regenerated (aged) catalyst in the reactor. In addition, the ratio of benzene to ethylene produced may also be controlled by adjusting the aromatization conditions and regeneration conditions in the disclosed process.

In general, in order to maintain a desired catalyst activity and product selectivity, fresh aromatization catalyst may be added to the regeneration zone or the fresh aromatization catalyst may be added and recycled with the spent catalyst. This fresh catalyst addition rate can be modified to achieve the desired ethane conversion and to control the ratio of benzene to ethylene produced in the product mixture. During operation, the aromatization catalyst level in the regenerator increases as fresh catalyst is added. Spent aromatization catalyst may be withdrawn from the regenerator to maintain the regenerator catalyst inventory between maximum and minimum capacity levels.

Due to continuous fresh catalyst addition and continuous withdrawal of catalyst (by either attrition loss or intentional withdrawal to maintain a constant inventory), the catalyst inventory has a wide age distribution. A portion of the catalyst inventory is relatively fresh (e.g., young), with high activity, while some of the catalyst circulating is spent (e.g., older), with relatively low activity and may have been in the process for weeks, months or even longer.

The alkane aromatization reaction is highly endothermic and requires a great amount of heat. At high temperatures, the aromatization catalysts rapidly deactivate due to formation of undesirable surface coke deposits which block access to the active sites of the catalyst. Catalyst from the reaction zone in the process of the presently disclosed subject matter may be deactivated rapidly and continuously cycled between the reaction zone and a regeneration zone where the accumulated coke is burned off of or otherwise removed from the catalyst to restore its activity. Thus, the process in the regeneration zone is exothermic and generates heat. Both the aromatization condition in the reaction zone and the regeneration condition in the regeneration zone have significant effects on the average catalyst activity of the catalyst inventory. For instance, a regeneration condition at higher temperature or/and high steam partial pressure can accelerate permanent catalyst deactivation.

According to an embodiment of the presently disclosed subject matter, a process for the production of benzene and ethylene from an alkane-containing gas stream may include step (a) contacting the alkane-containing gas stream, in a reaction zone of a reactor under alkane aromatization conditions, with an aromatization catalyst which may include a mixture of fresh catalyst and regenerated catalyst to produce an outlet stream comprising (i) spent catalyst and (ii) a product mixture comprising benzene and ethylene. In step (b) the spent catalyst may be separated from the product mixture in the outlet stream. In step (c), the separated spent catalyst may be regenerated in a regeneration zone under regeneration conditions to produce the regenerated catalyst. Next, in step (d), a selected amount of fresh catalyst may be added to the regeneration zone to produce the mixture of fresh catalyst and regenerated catalyst. In step (e), the mixture of fresh catalyst and regenerated catalyst may be recycled to the reaction zone. Further, a ratio of benzene to ethylene in the product mixture may be controlled in step (f) by modifying at least one selected of: the alkane aromatization conditions, the regeneration conditions, and the selected amount of fresh catalyst added to the regeneration zone in step (d).

Additional embodiments of the presently disclosed subject matter include the ability to vary the age distribution of the aromatization catalyst in the reaction zone. For example, the aromatization catalyst may include any combination of fresh, spent, and regenerated catalyst. In particular, it is not necessary that all of the spent catalyst be regenerated and recycled to the reaction zone. For example, a portion of the spent catalyst may be recycled back to the reaction zone (i.e., without being regenerated) and/or a portion of the spent catalyst may be regenerated and subsequently recycled to the reaction zone as described below.

In an aspect, a first portion of the spent catalyst may be regenerated to produce the regenerated catalyst. Fresh catalyst may be added to the regenerated catalyst and recycled back to the reaction zone. A second portion of the spent catalyst may be recycled back to the reaction zone (i.e., without being regenerated). In an embodiment of the disclosed subject matter, a process for the production of benzene and ethylene from an alkane-containing gas stream may include (a) contacting the alkane-containing gas stream, in a reaction zone of a reactor under alkane aromatization conditions, with an aromatization catalyst comprising recycled spent catalyst and a mixture of fresh catalyst and regenerated catalyst to produce an outlet stream comprising (i) spent catalyst and (ii) a product mixture comprising benzene and ethylene. In step (b), the spent catalyst may be separated from the product mixture in the outlet stream. Step (c) may include regenerating a first portion of the separated spent catalyst in a regeneration zone under regeneration conditions to produce the regenerated catalyst. Next, in step (d), a selected amount of fresh catalyst may be added to the regeneration zone to produce the mixture of fresh catalyst and regenerated catalyst. In step (e), the mixture of fresh catalyst and regenerated catalyst may be recycled to the reaction zone. In step (f) a second portion of the separated spent catalyst may be recycled to the reaction zone. Next in step (g), a ratio of benzene to ethylene in the product mixture may be controlled by modifying at least one selected from the group consisting of: the alkane aromatization conditions, the regeneration conditions, and the selected amount of fresh catalyst added to the regeneration zone in step (d).

In another aspect, a first portion of the spent catalyst may be regenerated and recycled back to the reaction zone. Fresh catalyst may be added to a second portion of the spent catalyst and recycled back to reaction zone. In an embodiment of the disclosed subject matter, the process for the production of benzene and ethylene from an alkane-containing gas stream may include (a) contacting the alkane-containing gas stream, in a reaction zone of a reactor under alkane aromatization conditions, with an aromatization catalyst comprising regenerated catalyst and a mixture of fresh catalyst and spent catalyst to produce an outlet stream comprising (i) spent catalyst and (ii) a product mixture comprising benzene and ethylene. In step (b) the spent catalyst may be separated from the product mixture in the outlet stream. Next in step (c) a first portion of the separated spent catalyst may be regenerated in a regeneration zone under regeneration conditions to produce the regenerated catalyst. Step (d) may include recycling the regenerated catalyst to the reaction zone. In step (e) a selected amount of fresh catalyst may be added to a second portion of the separated spent catalyst to produce the mixture of fresh catalyst and spent catalyst. Next, in step (f) the mixture of fresh catalyst and spent catalyst may be recycled to the reaction zone. In step (g), a ratio of benzene to ethylene in the product mixture may be controlled by modifying at least one of: the alkane aromatization conditions, the regeneration conditions, and the selected amount of fresh catalyst added to the second portion of the separated catalyst in step (e).

The alkane-containing gas stream may include at least one of ethane, propane, butane, and any combination thereof. Preferably, the majority of the gas stream is ethane. According to an embodiment, the alkane in the alkane-containing gas is ethane in the range of 75% vol. to 100% vol. The gas stream may contain in addition other open chain hydrocarbons containing between 3 and 8 carbon atoms as co-reactants. The gas stream may also contain a minor amount of methane. Specific examples of such additional co-reactants are propylene, isobutane, n-butenes and isobutene. The alkane-containing gas stream contains at least about 30 percent by weight of C2-4 hydrocarbons, and may contain at least about 50 percent by weight.

The alkane-containing gas stream that is fed to the reactor comprises in the range of from 50 to 100% vol. C2-C4 alkane, in the range of from 70 to 100% vol. C2-C4 alkane and in the range of from 75% vol. to 100% vol. C2-C4 alkane, based on the alkane-containing gas stream. Preferably, the balance of the alkane-containing gas may be methane, other C2+ alkanes, C2-C4 olefins, nitrogen, carbon dioxide and other non-hydrocarbon gases. The feed may contain small amounts of C2-C4 olefins, and no more than 5 to 10 weight percent. Too much olefin may cause an unacceptable amount of coking and deactivation of the catalyst. The alkane-containing gas stream may be, or be derived from, for instance, natural gas, natural gas liquids, LPG or associated gas, but also from refinery or petrochemical streams including waste streams.

According to an embodiment of the disclosed subject matter, the alkane aromatization reactor may be a moving bed reactor or a fluidized bed reactor. The alkane feed rate, expressed as gas hourly space velocity, may be in the range from 25 to 10000 h−1, from 40 to 8000 h−1, and from 70 to 6000 h−1. The conversion of alkanes in the alkane-containing gas stream may be carried out at a pressure in the range of from 0 barg to 3 barg. The conversion of alkanes in the alkane-containing gas stream may be carried out at a temperature in the range from 550 to 750° C., from 650 to 720° C., and from 670° C. to 700° C. The alkane aromatization conditions may also include an aromatization catalyst residence time in the reaction zone which is in the range from 1 minute to 60 minutes.

Any one of a variety of catalysts may be used to promote the reaction of lower alkanes to aromatic hydrocarbons (including but not limited to benzene) and ethylene. These catalysts generally include one or more metal components, a crystalline aluminosilicate or related component, and a binder component. In one aspect of the presently disclosed subject matter, the metal component(s) of the catalyst may be selected from vanadium, chromium, manganese, zinc, iron, cobalt, nickel, copper, gallium, germanium, niobium, molybdenum, ruthenium, rhodium, silver, tantalum, tungsten, rhenium, platinum and lead and mixtures thereof. The crystalline aluminosilicate component may include but is not limited to one or more zeolites selected from the ZSM family, including ZSM-5, ZSM-22, ZSM-8, ZSM-11, ZSM-12 or ZSM-35. The binder component, which is used to hold smaller crystalline aluminosilicate particles into larger aggregates of suitable size and density for use in fluidized-bed or moving-bed reactors, may be selected from a variety of materials used for this purpose including aluminas, silicas, metal oxides such as titanium dioxide, and clay materials.

Suitable catalyst are for instance are described in U.S. Pat. Nos. 4,899,006, 5,227,557, EP0244162, U.S. Pat. Nos. 7,186,871, 7,186,872, 8,871,990, 8,692,043, 8,772,563 and US20150321182 all of which are hereby incorporated by reference.

An example of a suitable catalyst to promote the reaction of lower alkanes to aromatic hydrocarbons is described in U.S. Pat. No. 4,899,006 which is herein incorporated by reference in its entirety. The catalyst composition described therein comprises an aluminosilicate having gallium deposited thereon and/or an aluminosilicate in which cations have been exchanged with gallium ions. The molar ratio of silica to alumina is at least 5:1.

Another catalyst which may be used in the process of the presently disclosed subject matter is described in EP0244162. This catalyst comprises the catalyst described in the preceding paragraph and a Group VIII metal selected from rhodium and platinum. The aluminosilicates are said to be MFI or MEL type structures, but may be selected from ZSM-5 (MFI), ZSM-8 MFI/MEL), ZSM-11 (MEL), ZSM-12 (MTW) or ZSM-35 (FER).

Other catalysts which may be used in the presently disclosed process are described in U.S. Pat. Nos. 7,186,871 and 7,186,872, both of which are herein incorporated by reference in their entirety. The first of these patents describes a platinum containing ZSM-5 crystalline zeolite synthesized by preparing the zeolite containing the aluminum and silicon in the framework, depositing platinum on the zeolite and calcining the zeolite. The second patent describes such a catalyst which contains gallium in the framework and is essentially aluminum-free.

In an aspect, the catalyst may be comprised of a zeolite, a noble metal of the platinum family to promote the dehydrogenation reaction, and a second inert or less active metal which will attenuate the tendency of the noble metal to catalyze hydrogenolysis of the C2 and higher hydrocarbons in the feed to methane and/or ethane. Attenuating metals which can be used include those described below.

Additional catalysts which may be used in the presently disclosed process include those described in U.S. Pat. No. 5,227,557, hereby incorporated by reference in its entirety. These catalysts contain an MFI zeolite plus at least one noble metal from the platinum family and at least one additional metal chosen from the group consisting of tin, germanium, lead, and indium.

Another example of a catalyst for use in presently disclosed process is described in U.S. Pat. No. 8,871,990. This publication is hereby incorporated by reference in its entirety. The publication describes a catalyst comprising: (1) 0.005 to 0.1 wt % (% by weight) platinum, based on the metal, 0.01 to 0.05 wt %, (2) an amount of an attenuating metal selected from the group consisting of tin, lead, and germanium which is not more than 0.2 wt % of the catalyst, based on the metal and wherein the amount of platinum may be no more than 0.02 wt % more than the amount of the attenuating metal; (3) 10 to 99.9 wt % of an aluminosilicate, preferably a zeolite, based on the aluminosilicate, 30 to 99.9 wt %, and selected from the group consisting of ZSM-5, ZSM-11, ZSM-12, ZSM-23, or ZSM-35, and may be converted to the H+ form, and may have a SiO2/Al2O3 molar ratio of from 20:1 to 80:1, and a binder, for example selected from silica, alumina and mixtures thereof.

Another suitable catalyst for use in this presently disclosed subject matter is described in US20110021853. This patent application is hereby incorporated by reference in its entirety. The application describes a catalyst comprising: (1) 0.005 to 0.1 wt % (% by weight) platinum, based on the metal, 0.01 to 0.06 wt %, and 0.01 to 0.05 wt %, (2) an amount of iron which is equal to or greater than the amount of the platinum but not more than 0.50 wt % of the catalyst, not more than 0.20 wt % of the catalyst, and not more than 0.10 wt % of the catalyst, based on the metal; (3) 10 to 99.9 wt % of an aluminosilicate, preferably a zeolite, based on the aluminosilicate, and 30 to 99.9 wt %, and selected from the group consisting of ZSM-5, ZSM-11, ZSM-12, ZSM-23, or ZSM-35, and may be converted to the H+ form, and may have a SiO2/Al2O3 molar ratio of from 20:1 to 80:1, and (4) a binder, selected from silica, alumina and mixtures thereof.

Another example of a catalyst for use in the presently disclosed process is described in US20090209794. This publication is hereby incorporated by reference in its entirety. The publication describes a catalyst comprising: (1) 0.005 to 0.1 wt % (% by weight) platinum, based on the metal, 0.01 to 0.05% wt, and 0.02 to 0.05% wt, (2) an amount of gallium which is equal to or greater than the amount of the platinum, no more than 1 wt %, and no more than 0.5 wt %, based on the metal; (3) 10 to 99.9 wt % of an aluminosilicate, preferably a zeolite, based on the aluminosilicate, 30 to 99.9 wt %, and selected from the group consisting of ZSM-5, ZSM-11, ZSM-12, ZSM-23, or ZSM-35, may be converted to the H+ form, and may have a SiO2/Al2O3 molar ratio of from 20:1 to 80:1, and (4) a binder, selected from silica, alumina and mixtures thereof.

Still another example catalyst is disclosed in US20150321182, which catalyst comprises from about 0.005 to about 0.09% wt platinum, basis the metal. The platinum is highly active in terms of catalyzing not only the desired dehydroaromatization reaction but also an undesired hydrogenolysis reaction leading to lower-value byproduct methane, so it is best if its concentration in the catalyst not be more than 0.1% wt because otherwise too much methane will be produced. In one embodiment from about 0.005 to about 0.05% wt of platinum is used.

An attenuating metal or metals may also be added to the catalyst of the presently disclosed subject matter. While the attenuating metal may have catalytic activity in its own right, its main function is to moderate the catalytic activity of platinum so as to reduce the production of less-valuable methane byproduct. Examples of suitable attenuating metals include but are not limited to tin, lead, germanium, and gallium. The attenuating metal comprises not more than about 0.5% wt of the catalyst, basis the metal, not more than about 0.2% wt and not more than about 0.1% wt of the attenuating metal is utilized because more than that can cause the overall conversion to aromatics to become too low for commercial use.

The catalyst also comprises from about 10 to about 99.9% wt of one or more aluminosilicate materials, from about 30 to about 99.9% wt, basis the aluminosilicate(s). The aluminosilicates may have a silicon dioxide:aluminum trioxide (SiO2:Al2O3) molar ratio of from about 20 to about 80. The aluminosilicates may be zeolites having the MFI or MEL type structure and may be ZSM-5, ZSM-8, ZSM-11, ZSM-12 or ZSM-35. The zeolite or zeolite mixture may be converted to H+ form to provide sufficient acidity to help catalyze the dehydroaromatization reaction. This can be accomplished by calcining the ammonium form of the zeolite in air at a temperature of at least about 400° C.

The aromatization catalyst may be in the form of cylindrical pellets, rings, spheres, and the like. As an example, in a fluidized bed reactor operation, the catalyst may be a particulate material comprising particles, and each particle shape may be spherical. The spherical catalyst particulate could be prepared by any method known to those skilled in the art. The spherical catalyst may be prepared via spray drying of zeolite containing sols of appropriate concentration and composition. The zeolite containing sol may optionally contain binder. The spherical catalyst particle may have a predominant particle size or diameter that makes it suitable for a particular reactor type, such as a fluidized bed reactor. The particle diameter of the catalyst may be selected to be in the range of 1-300 microns. In an aspect, the spherical catalyst may have a particle diameter in the range of 5 to 180 microns, and may have an average particle size of 50 to 120, and 60 to 90 microns. The average particle size may refer to the weight average particle size, number average particle size, and the like. In general, approximately 95% of the aromatization catalyst particles may fall within the size ranges provided herein.

In step (b) the spent catalyst may be separated from the product mixture in the outlet stream. The spent aromatization catalyst has to be regenerated to restore its aromatization activity to a level similar to its original activity. It is well known that the alkane-containing gas aromatization catalysts form coke during the reaction. Accumulation of coke on the surface of the catalyst gradually covers the active aromatization sites of the catalyst resulting in gradual reduction of its activity. Therefore, the spent (coked) catalyst has to be removed at certain carefully chosen frequencies from the reaction zone of the reactor and regenerated in a regeneration zone.

Next, in step (c), the separated spent catalyst may be regenerated in a regeneration zone under regeneration conditions to produce the regenerated catalyst. The regeneration of the catalyst can be carried out by any method known to those skilled in the art. For example, two possible regeneration methods are hot hydrogen stripping and oxidative burning at temperatures sufficient to remove the coke from the surface of the catalyst. The regeneration conditions may include a temperature in the range of from 650° C. to 750° C., and 650° C. to 700° C. The regeneration conditions may also include a pressure in the range of from 0 barg to 5 barg, and 1 barg to 3 barg. The regeneration conditions may also include a spent catalyst residence time in the regeneration zone which is in the range from 30 seconds to 30 minutes. In an aspect, the regeneration conditions may also include water partial pressure in the range of from 0 bar to 0.1 bar and oxygen partial pressure in the range of from 0 bar to 0.5 bar.

In step (d), a selected amount of fresh catalyst may be added to the regeneration zone to produce the mixture of fresh catalyst and regenerated catalyst. Next, in step (e), the mixture of fresh catalyst and regenerated catalyst may be recycled to the reaction zone. As mentioned above, in order to maintain a desired catalyst activity and product selectivity, fresh aromatization catalyst may be added to the regeneration zone. This selected amount of fresh catalyst that is added to the regeneration zone can be modified to achieve the desired ethane conversion and to control the ratio of benzene to ethylene produced in the product mixture. For example, in order to increase the ratio of benzene to ethylene in the product mixture the selected amount of fresh catalyst added in step (d) may be added. On the other hand, in order to decrease the ratio of benzene to ethylene in the product mixture, the selected amount of fresh catalyst added in step (d) may be decreased. In general, as the number of feed/coke burn cycles increases (i.e., the age of the aromatization catalyst is relatively older), the benzene yield decreases while the ethylene yield increases. This property of the aromatization catalyst enables increasing or decreasing the ratio of benzene to ethylene yields by adjusting the proportions of fresh and variously-aged (regenerated) catalyst in the reaction zone of the reactor.

In step (f), the ratio of benzene to ethylene in the product mixture may be controlled by modifying the alkane aromatization conditions, the regeneration conditions, and the selected amount of fresh catalyst added to the to the regeneration zone in step (d). For example, the alkane aromatization conditions may be modified by adjusting the temperature, pressure, feed rate, and/or residence time in order to control the ratio of benzene to ethylene. Similarly, the regeneration conditions may be modified to control the ratio of benzene to ethylene by adjusting the temperature, pressure, and/or space velocity in order to control factors that affect catalyst performance such as the amount of surface coke, the dispersion of the active metal components, and the rate of destruction of active acidic sites in the aluminosilicate components.

EXAMPLES

Example 1

This example is provided for illustrative purposes only and is not intended to limit the scope of the invention. In this example, the presently disclosed subject matter is demonstrated by presenting the results of bench-scale performance tests of 20-gram catalyst charges containing varying proportions of fresh (never-before-tested) and hydrothermally-aged catalyst sample. Hydrothermal (high-temperature steam) treatment is a well-established accelerated aging method to simulate the effects of many cycles of feed exposure and regeneration (coke burnoff) on catalyst performance in numerous applications such as fluid catalytic cracking. Wide ranges of steaming temperatures and times have been used depending on the reaction(s) being catalyzed, the process conditions, and the type of zeolite(s) present in the catalyst. This subject is discussed in a chapter by E. L. Moorehead, J. B. McLean, and W. A. Cronkright entitled "Microreactivity Evaluation of FCC Catalysts in the Laboratory: Principles, Approaches and Applications," pages 223-255 of Fluid Catalytic Cracking: Science & Technology (J. S. Magee & J. J. Mitchell, Jr., Eds., Elsevier Science Publishers B.V., 1993), and in a chapter by G. W. Young, entitled "Realistic Assessment of FCC Catalyst Performance in the Laboratory," pages 257-282 of Fluid Catalytic Cracking: Science & Technology (J. S. Magee & J. J. Mitchell, Jr., Eds., Elsevier Science Publishers B.V., 1993), both of which are hereby incorporated by reference in their entirety. The steaming conditions used in the example below do not necessarily represent an optimum simulated catalyst aging regime for any particular application but are merely intended to illustrate the concept of the presently disclosed subject matter.

Catalyst A was prepared on a spray-dried powder material containing 55% wt of CBV 2314 ZSM-5 zeolite (23:1 molar SiO2/Al2O3 ratio, available from Zeolyst International), 25% wt silica, and 20% wt clay. For clarity, CBV 2314 zeolite powder is commercially available while the 55/25/20% wt zeolite/silica/clay spray-dried powder is not commercially available. To reduce the level of sodium impurity and increase the acidity of this material, a sample was combined with a two-fold excess (be weight) of a 50% solution of ammonium nitrate in deionized water at room temperature for about 15 minutes, then filtered, and washed with an equal weight of deionized water. This entire process was repeated. After the second washing with deionized water, the filter cake was dried at 120° C. overnight. The sodium level on this treated sample (measured by inductively coupled plasma jet analysis) was 122 ppm. Particle size distribution data for this powder are provided in Table 1. Samples of this powder were calcined to 425° C. to remove residual moisture and ammonia prior to use in catalyst preparation. The resulting powder contained ZSM-5 zeolite in its ion-exchanged, acidic form.

TABLE 1

Particle size distribution data for a 650° C.-calcined sample of ion-exchanged, spray-dried powder used to make catalyst A.

| Percentile | Particle Size, Microns |
| --- | --- |
| 10 | 45.6 |
| 20 | 61.2 |
| 30 | 72.8 |
| 40 | 83.1 |
| 50 | 93.4 |
| 60 | 104.5 |
| 70 | 117.5 |
| 80 | 134.5 |
| 90 | 162.5 |
| 95 | 190.6 |

Platinum and gallium were deposited on a 500-g sample of the above ion-exchanged, spray-dried powder by first combining appropriate amounts of stock solutions of tetraammine platinum nitrate and gallium (III) nitrate, diluting this mixture with deionized water to a volume just sufficient to fill the pores of the powder, and impregnating the powder with this solution at room temperature and atmospheric pressure. The impregnated sample was aged at room temperature for about two hours, then calcined to 650° C. in air using the following temperature program: ramp from 100 to 650° C. at 3° C./minute, hold at 650° C. for 3 hours, then cool to 100° C. Target platinum and gallium levels on the finished catalyst were 50 ppmw and 0.12% wt, respectively.

To determine actual platinum and gallium levels on Catalyst A, a sample of the catalyst was calcined at 550° C. to drive off residual moisture to render a loss on ignition (LOI) percentage. A known mass of the untreated ground catalyst, corrected by LOI percentage, was digested using closed vessel microwave acid digestion involving nitric, hydrochloric, and hydrofluoric acids. The solution was diluted to a known volume with deionized water and then analyzed for gallium and platinum by inductively coupled plasma emission analysis and inductively coupled plasma emission/mass spectrometry analysis, respectively. Measured platinum and gallium contents for Catalyst A, based on the weight of the 550° C.-calcined sample, were 38+2 ppm and 1040+30 ppm, respectively.

A 60-g sample of Catalyst A was subjected to hydrothermal treatment at ambient pressure with a 50/50% mol/mol steam/nitrogen feed. Treatment was initiated by heating the sample in a quartz tube with flowing nitrogen at 20.4 liters per hour from ambient temperature to 700° C. at a heating rate of 180° C. per hour. When the temperature reached 260° C., water was introduced at a rate of 15 g/hr. Treatment was continued for 4 hours after reaching the target temperature of 700° C. Throughout the test, the direction of steam/nitrogen flow through the tube was switched every 30 minutes. After 4 hours of treatment at 700° C., water addition was stopped, and the sample was cooled down to ambient temperature under flowing nitrogen. This steam-treated catalyst sample is hereinafter designated as Catalyst A/S.

Total catalyst charges of 20 grams, containing varying proportions of Catalyst A and Catalyst A/S, were loaded into quartz reactor tubes (16 mm i.d.) and loaded into bench-scale reactors connected to an automated gas flow system. The reactors were configured for upflow operation to enable catalyst pretreatment, performance testing, and regeneration operations in fluidized-bed mode.

Prior to performance testing, all catalyst charges were pretreated in situ at atmospheric pressure according to the following protocol:
(a) calcination with air at 10 liters per hour (L/hr), during which the reactor wall temperature was ramped from 25 to 510° C. in 12 hours, held at 510° C. for 4 hours, increased to 621° C. in 1 hr, then held at 621° C. for 30 minutes;
(b) nitrogen purge at 10 L/hr, 621° C. for 20 minutes;
(c) hydrogen reduction at 10 L/hr for 1.5 hours, during which time the reactor wall temperature was increased to 700° C. The 700° C. reactor wall temperature was maintained during all subsequent catalyst performance testing and regeneration operations.

At the end of pretreatment, the hydrogen flow was shut off, and 100% ethane feed was introduced at ambient pressure at a flow rate of 5.6 L/hr for 30 minutes, followed by nitrogen at 10 L/hr for 20 minutes, air at 10 L/hr for 30 minutes, then nitrogen at 10 L/hr for 20 minutes, for a total feed exposure/air regeneration cycle time of 100 minutes. This 100-minute operational cycle was repeated automatically. Online sampling and gas chromatographic (GC) analysis of the total reactor outlet stream occurred 15 minutes after feed introduction during the first feed/regeneration cycle and again at 15 minutes after feed introduction every sixth cycle thereafter.

Based on reactor outlet composition data obtained from the online GC analyses, ethane conversion and hydrocarbon product selectivities were calculated according to the following formulas:

$$\text{ethane conversion, \%} = 100 \times (100 - \text{\% wt ethane in reactor outlet stream})/(\text{\% wt ethane in feed})$$

$$\text{selectivity to product } Y \text{ (other than ethane), \% wt} = 100 \times (\text{\% wt } Y \text{ in reactor outlet stream})/(\text{ethane conversion, \%})$$

Five performance tests were conducted according to the above protocol with 20-g catalyst charges containing varying proportions of fresh Catalyst A and steamed Catalyst A/S. Table 2 contains the amounts of Catalysts A and A/S used in each test and the ethane conversion and product selectivity data computed from the results of online GC analysis of operational cycle number 13 from each test. By the time the operational cycle 13 GC sample was taken, the catalyst charge had been exposed to ethane feed for a total of 6.25 hours and to 12 regenerations (coke burns) lasting 30 minutes each.

TABLE 2

Performance test data

| | Performance Test Number | | | | |
|---|---|---|---|---|---|
| | 1 | 2 | 3 | 4 | 5 |
| Amount of Catalyst A, G | 0 | 5 | 10 | 15 | 20 |
| Amount of Catalyst A/S, G | 20 | 15 | 10 | 5 | 0 |
| Ethane Conversion, % | 43.87 | 55.35 | 66.19 | 68.93 | 72.63 |
| Product Selectivities, % Wt | | | | | |
| Hydrogen | 6.45 | 8.70 | 9.12 | 9.39 | 8.98 |
| Methane | 8.77 | 12.07 | 13.17 | 16.27 | 19.09 |
| Ethylene | 66.58 | 26.56 | 20.37 | 8.81 | 7.77 |
| Propylene | 3.20 | 2.67 | 1.67 | 1.21 | 0.92 |
| Propane | 0.53 | 0.82 | 0.52 | 0.72 | 0.58 |
| $C_4$ Hydrocarbons | 1.80 | 1.16 | 0.69 | 0.28 | 0.21 |
| $C_5$ Hydrocarbons | 0.69 | 0.09 | 0.05 | 0.02 | 0.01 |
| Benzene | 6.46 | 28.99 | 32.04 | 38.52 | 40.59 |
| Toluene | 2.78 | 13.94 | 14.39 | 16.47 | 15.08 |
| $C_8$ Aromatics | 0.94 | 1.80 | 2.06 | 2.17 | 1.99 |
| $C_{9+}$ Aromatics | 1.80 | 3.20 | 5.92 | 6.14 | 4.78 |
| Total Aromatics | 11.98 | 47.93 | 54.42 | 63.30 | 62.44 |
| Benzene/Ethylene Selectivity Ratio | 0.10 | 1.09 | 1.57 | 2.37 | 5.22 |

As shown in Table 2, the ethylene selectivity under these test conditions decreases from 66.58% wt to 7.77% wt, and the benzene selectivity rises from 6.46% wt to 40.59% wt, as the percentage of Catalyst A in the total catalyst charge increases from 0 to 100%. Thus, the ratio of benzene selectivity to ethylene selectivity ranges from 0.10 to 5.22 as the proportion of Catalyst A relative to Catalyst A/S is increased. In commercial operation, the relative proportions of fresh (or less-aged) catalyst and spent (or "equilibrated") catalyst in the reactor can be controlled by changing the rate of addition of fresh catalyst and removal of spent catalyst, which will in turn provide the operator with flexibility to vary the relative amounts of benzene and ethylene produced.

The aforementioned process provides for the ability to control a ratio of benzene to ethylene produced by modifying at least one of: the alkane aromatization conditions, the regeneration conditions, and the selected amount of fresh catalyst added to the regeneration zone. This results in significantly higher and economically more attractive alkane-containing gas stream conversion as well as benzene and aromatics yields. As discussed above, the presently disclosed subject matter provides for the ability to utilize an aromatization catalyst that enables the production of different relative amounts of benzene and ethylene as a function of catalyst age. In addition, the process of the presently disclosed subject matter utilizes an aromatization catalyst that enables proportionately greater benzene production along with ethylene, at a lower temperature than that typically used in ethane crackers (680-700° C. vs. 750-800° C.). For the co-production of benzene and ethylene, the presently disclosed process provides the ability to add fresh catalyst and remove spent catalyst during reactor operation so that relative yields of benzene and ethylene may be altered. Because the ratio of benzene to ethylene production by the aromatization catalyst declines as the aromatization catalyst ages, the disclosed process provides flexibility for altering desired relative yields of benzene and ethylene by adjusting the relative amounts of fresh and regenerated (aged) catalyst in the reactor. Therefore, the disclosed subject matter allows for the commercialization of an economically attractive direct, non-oxidative alkane-containing gas stream aromatization process.

That which is claimed is:

1. A process for the production of benzene and ethylene from an alkane-containing gas stream, which alkane-containing gas stream contains at least one alkane selected from the group consisting of ethane, propane or butane, comprising:
   (a) contacting the alkane-containing gas stream, in a reaction zone of a reactor under alkane aromatization conditions, with an aromatization catalyst comprising a mixture of fresh catalyst and regenerated catalyst to produce an outlet stream comprising (i) spent catalyst and (ii) a product mixture comprising benzene and ethylene,
   (b) separating the spent catalyst from the product mixture in the outlet stream,
   (c) regenerating the separated spent catalyst in a regeneration zone under regeneration conditions to produce the regenerated catalyst,
   (d) adding a selected amount of fresh catalyst to the regeneration zone to produce a mixture of fresh catalyst and regenerated catalyst,
   (e) recycling the mixture of fresh catalyst and regenerated catalyst to the reaction zone, and
   (f) controlling the ratio of benzene to ethylene in the product mixture by modifying at least one selected from the group consisting of: the alkane aromatization conditions, the regeneration conditions, and the selected amount of fresh catalyst added to the regeneration zone in step (d),
   wherein the alkane aromatization conditions may be modified by adjusting the temperature, pressure, feed rate, and/or residence time and the regeneration conditions may be modified by adjusting the temperature, pressure, and/or space velocity.

2. A process for the production of benzene and ethylene from an alkane-containing gas stream, which alkane-containing gas stream contains at least one alkane selected from the group consisting of ethane, propane or butane, comprising:
   (a) contacting the alkane-containing gas stream, in a reaction zone of a reactor under alkane aromatization conditions, with an aromatization catalyst comprising recycled spent catalyst and a mixture of fresh catalyst and regenerated catalyst to produce an outlet stream comprising (i) spent catalyst and (ii) a product mixture comprising benzene and ethylene,
   (b) separating the spent catalyst from the product mixture in the outlet stream,
   (c) regenerating a first portion of the separated spent catalyst in a regeneration zone under regeneration conditions to produce the regenerated catalyst,
   (d) adding a selected amount of fresh catalyst to the regeneration zone to produce a mixture of fresh catalyst and regenerated catalyst,
   (e) recycling the mixture of fresh catalyst and regenerated catalyst to the reaction zone,
   (f) recycling a second portion of the separated spent catalyst to the reaction zone,
   and
   (g) controlling the ratio of benzene to ethylene in the product mixture by modifying at least one selected from the group consisting of: the alkane aromatization conditions, the regeneration conditions, and the selected amount of fresh catalyst added to the regeneration zone in step (d),
   wherein the alkane aromatization conditions may be modified by adjusting the temperature, pressure, feed rate, and/or residence time and the regeneration conditions may be modified by adjusting the temperature, pressure, and/or space velocity.

3. A process for the production of benzene and ethylene from an alkane-containing gas stream, which alkane-containing gas stream contains at least one alkane selected from the group consisting of ethane, propane or butane, comprising:
  (a) contacting the alkane-containing gas stream, in a reaction zone of a reactor under alkane aromatization conditions, with an aromatization catalyst comprising regenerated catalyst and a mixture of fresh catalyst and spent catalyst to produce an outlet stream comprising (i) spent catalyst and (ii) a product mixture comprising benzene and ethylene,
  (b) separating the spent catalyst from the product mixture in the outlet stream,
  (c) regenerating a first portion of the separated spent catalyst in a regeneration zone under regeneration conditions to produce the regenerated catalyst,
  (d) recycling the regenerated catalyst to the reaction zone,
  (e) adding a selected amount of fresh catalyst to a second portion of the separated spent catalyst to produce a mixture of fresh catalyst and spent catalyst,
  (f) recycling the mixture of fresh catalyst and spent catalyst to the reaction zone, and
  (g) controlling the ratio of benzene to ethylene in the product mixture by modifying at least one selected from the group consisting of: the alkane aromatization conditions, the regeneration conditions, and the selected amount of fresh catalyst added to the second portion of the separated catalyst in step (e), wherein the alkane aromatization conditions may be modified by adjusting the temperature, pressure, feed rate, and/or residence time and the regeneration conditions may be modified by adjusting the temperature, pressure, and/or space velocity.

4. The process of claim 1, further comprising increasing the ratio of benzene to ethylene in the product mixture by increasing the selected amount of fresh catalyst added in step (d).

5. The process of claim 1, further comprising decreasing the ratio of benzene to ethylene in the product mixture by decreasing the selected amount of fresh catalyst added in step (d).

6. The process of claim 1, wherein the alkane aromatization conditions comprise a temperature in the range of from 550° C. to 750° C.

7. The process of claim 1, wherein the alkane aromatization conditions comprise an aromatization catalyst residence time in the reaction zone which is in the range from 1 minute to 60 minutes.

8. The process of claim 1, wherein the regeneration conditions comprise a temperature in the range of from 650° C. to 750° C.

9. The process of claim 1, wherein the regeneration conditions comprise a spent catalyst residence time in the regeneration zone which is in the range from 30 seconds to 30 minutes.

10. The process of claim 1, wherein the aromatization catalyst comprises a zeolite selected from the group consisting of ZSM-5, ZSM-22, ZSM-8, ZSM-11, ZSM-12 or ZSM-35.

* * * * *